United States Patent [19]

Sandler

[11] Patent Number: 5,117,051
[45] Date of Patent: May 26, 1992

[54] PREPARATION OF ALKANEDISULFONIC ACIDS

[75] Inventor: Stanley R. Sandler, Springfield, Pa.

[73] Assignee: Atochem North America, Inc., Philadelphia, Pa.

[21] Appl. No.: 776,712

[22] Filed: Oct. 15, 1991

Related U.S. Application Data

[63] Continuation of Ser. No. 287,518, Dec. 19, 1988, abandoned, which is a continuation of Ser. No. 56,579, Jun. 1, 1987, abandoned.

[51] Int. Cl.$^5$ ............................................ C07C 303/00
[52] U.S. Cl. ................................... 562/101; 562/123
[58] Field of Search ............................... 562/101, 123

[56] References Cited

U.S. PATENT DOCUMENTS 2,493,038  1/1950  Snyder et al.
2,842,589  11/1958  Crowder et al.

OTHER PUBLICATIONS

Gilbert, Sulfonation and Related Reactions (1965), p. 18.
W. Muthmann, *Ber. d. deutsch. chem. Ges.*, (1898) 31;1880.
G. Schroeter, *Ber. d. deustsch. chem. Ges.*, (1898) 31;2189-90 and (1905) 38;3389-3393.
*Annalen der Chemie*, (1898) 303;114-132 and (1919) 418;161-257.
H. J. Backer, *Rec. Trav. Chem*, (1929), 48;949-52.
William E. Truce, et al., "Sulfonation of Ketones and Aldehydes," *J. Amer. Chem. Soc.*, 72:2740-3 (1950).
Arthur W. Weston, et al., "The Reaction of Chlorosulfonic Acid with Acetophenone. New Synthesis of a Cyclic Ketosulfone," *J. Amer. Chem. Soc.*, 61:389-91 (1939).
Everett E. Gilbert, *Sulfonation and Related Reactions*, Interscience, New York (1965), pp. 18-20, 42-46.
L. P. Ryadneva et al., Pressure of Saturated $HSO_3Cl$ Vapor, translated from Zhurnal Prikladnof Khimii, vol. 36, No. 11, pp. 2340-2345 (1963).
Kirk-Othmer, "Castor Oil to Chlorosulfuric Acids," *Encyclopedia of Chemical Technology*, 3rd Ed., vol. 5, pp. 873-880 (1979), (John Wiley & Sons).
DuPont Technical Bulletin No. E-52057, "Chlorosulfonic Acid—Properties, Uses, Storage and Handling" (Nov. 1982).
K. E. Jackson, "Smoke-Forming Chemicals," *Chemical Reviews* 25:67, 81-100 (1939).

Primary Examiner—Alan Siegel
Attorney, Agent, or Firm—Panitch Schwarze Jacobs & Nadel

[57] ABSTRACT

Alkanedisulfonic acids, particularly methanedisulfonic acid (methionic acid), can be prepared by reacting the corresponding alkanesulfonic acid with chlorosulfonic acid. The reaction is carried out by heating the reactants with agitation, preferably under substantially anhydrous conditions in the presence of oxygen and at substantially atmospheric pressure. Particularly good yields are obtained using an activated carbon co-catalyst.

20 Claims, No Drawings

PREPARATION OF ALKANEDISULFONIC ACIDS

CROSS-REFERENCE TO RELATED APPLICATIONS

This is a continuation application of my copending patent application Ser. No. 07/287,518, filed Dec. 19, 1988, abandoned, which is a continuation of U.S. patent application Ser. No. 07/056,579, filed Jun. 1, 1987, abandoned.

FIELD OF THE INVENTION

The present invention is directed to methods of preparation of alkanedisulfonic acids, particularly methanedisulfonic acid (MDSA), which is also known as methionic acid.

BACKGROUND OF THE INVENTION

The preparation of methanedisulfonic acid has been known since at least the turn of the century, but the various methods reported in the literature have serious deficiencies which make the prior methods uneconomical or impractical. Initially, MDSA was prepared by reacting acetylene with fuming sulfuric acid to yield acetaldehydedisulfonic acid (O=CH—CH(SO$_3$H)$_2$) as an intermediate product which was then decomposed to give methionic acid and other by-products; W. Muthmann, *Ber. d. deutsch. chem. Ges.*, 31;1880 (1898); G. Schroeter, *Ber. d. deutsch. chem. Ges.*, 31;2189-90 (1898) and 38;3389-3393 (1905), *Annalen der Chemie.* 303;114-132 (1898) and 418;161-257 (1919). This method has the disadvantage of requiring the handling of acetylene in dilute form. Acetylene is known to be explosive in concentrated form and is extremely reactive. It cannot be shipped long distances, and for large-scale operations must be used near its point of manufacture.

In 1929 it was reported that the acetylene method had been repeated and produced a poor yield of product, H. J. Backer, *Rec. Trav. Chem.*, 48;949-52 (1929). Backer also reported in the same reference that he obtained MDSA by heating methylene dichloride with potassium sulfite dissolved in water in an autoclave at 150-160 degrees Centigrade for two hours. The potassium salt is converted to the barium salt and the free acid obtained from it using sulfuric acid. This procedure has the disadvantage of requiring an autoclave and the additional steps involving salts which must be converted to the free acid.

In 1950 J. C. Snyder and A. V. Grosse disclosed in U.S. Pat. No. 2,493,038 a method (example IV) in which methane was autoclaved with sulfur trioxide at 840 psi and 260 degrees Centigrade for 1.5 hours using mercuric sulfate as a catalyst to give a mixture of methanesulfonic acid, MDSA and methanol (present as the ester). This method has the disadvantages of requiring high temperatures and pressures along with the difficult to handle sulfur trioxide and methane gases.

In 1958 J. A. Crowder and E. E. Gilbert disclosed in U.S. Pat. No. 2,842,589 that MDSA could be prepared by reacting methanesulfonic acid with sulfur trioxide, but repetition of this method in our laboratory yielded MDSA contaminated by many by-products. As with the method of Snyder et al, this method has the disadvantage of requiring the handling of sulfur trioxide, which is difficult due to its narrow liquid temperature range (boiling point 44.8 degrees Centigrade and freezing point 17 degrees Centigrade). In addition, trace amounts of water or sulfuric acid act as polymerization catalysts for liquid sulfur trioxide, producing polymers having elevated melting points.

In view of the serious deficiencies of the prior art methods described above, it would be desirable to have a simple method for producing methanedisulfonic acid and other alkanedisulfonic acids in sufficient yields to be economically viable.

SUMMARY OF THE INVENTION

According to the present invention alkanedisulfonic acids may be prepared by reacting chlorosulfonic acid with an alkanesulfonic acid to yield a mixture of the alkanedisulfonic acid with alkanesulfonic acid and alkanesulfonyl chloride. The reaction is preferably carried out under substantially anhydrous conditions in the presence of oxygen (air) at substantially atmospheric pressure and temperatures in the range of about 70 to 160 degrees Centigrade. Still more preferably, the reaction is carried out in the presence of an activated carbon catalyst.

DETAILED DESCRIPTION OF PREFERRED EMBODIMENTS

Although the preparation method of the invention applies generally to the preparation of alkanedisulfonic acids from the reaction of chlorosulfonic acid with an alkanesulfonic acid, the method will be described below with specific reference to the preparation of methanedisulfonic acid from the reaction of chlorosulfonic acid with methanesulfonic acid. It will be understood that other alkanesulfonic acids, particularly lower (one to six carbon atoms) alkanesulfonic acids, such as ethanesulfonic acid, propanesulfonic acid, etc. may be reacted with the chlorosulfonic acid to yield the corresponding alkanedisulfonic acids.

The reaction of chlorosulfonic acid with methanesulfonic acid may be represented by the following equation:

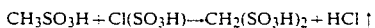

$$CH_3SO_3H + Cl(SO_3H) \rightarrow CH_2(SO_3H)_2 + HCl \uparrow$$

This reaction should be carried out under anhydrous conditions since chlorosulfonic acid reacts vigorously with water. Methanesulfonic acid and chlorosulfonic acid may be prepared by methods well known in the art, and both are available commercially from several sources. For example, anhydrous methanesulfonic acid (100%) is available commercially from Pennwalt Corporation. Chlorosulfonic acid is typically available in 95-100% purity grade, with the principal impurities being hydrochloric and sulfuric acids which are formed when chlorosulfonic acid is contaminated with water.

The reaction is preferably carried out at substantially atmospheric pressure in the presence of air or other oxygen containing atmosphere. Thus, when the reaction was carried out under pressure and in the absence of air (see Example 4 below), no MDSA was formed, but methanesulfonyl chloride was produced instead. Of course, pressures somewhat above or below atmospheric pressure would be expected to produce some of the desired product, but at slower reaction rates and reduced yields.

The preparation method involves heating a mixture of methanesulfonic acid and chlorosulfonic acid to a temperature in the range of about 70 degrees Centigrade to about 160 degrees Centigrade, and preferably about 100 to 160 degrees Centigrade. At these temperatures the reaction proceeds to equilibrium in about one hour or less. The reaction proceeds with simple agitation (e.g., stirring) and heating in the liquid state without the need of solvents or diluents, and is complete when the evolution of hydrogen chloride ceases.

The reactants may be present in an equimolar ratio or with excess of either of the reactants. Thus, the mole ratio of chlorosulfonic acid to methanesulfonic acid can range from about 0.5:1 to about 3:1, and is preferably about 1:1 to about 1.5:1. As shown in Example 5 below, an excess of chlorosulfonic acid does not appear to improve the yield of MDSA and results in a larger percentage of unknowns.

According to a particularly preferred embodiment of the present invention, the preparation method is carried out in the presence of a cocatalyst (in addition to oxygen). The cocatalyst may be an activated carbon, preferably a high surface area activated carbon. The term "activated carbon" as used herein will be understood in its broadest sense to include commercially available activated carbons, carbonaceous materials which have been pyrolyzed or destructively distilled, as well as carbonaceous materials which can be carbonized (hydrogen and oxygen burned off to leave essentially only carbon) in situ. As indicated in Example 2 below, 0.1 grams of activated carbon functioned to catalyze a reaction sufficient to yield 0.1 mole (theoretical) of product. It is believed that about 0.5 to 2 grams of activated carbon catalyst per mole of theoretical product will be satisfactory.

While commercially available activated carbon and carbonized cork are illustrated as cocatalysts in the examples below, it is believed that any source of carbon which can be carbonized would be effective as the activated carbon cocatalyst. Thus, in Example 1 a piece of cork fell into the reaction mixture and was apparently carbonized by the acid reaction mixture, in effect forming activated carbon in situ and functioning as a catalyst for the reaction. Similarly, in Example 5 no cork fell into the reaction mixture, but the reaction mixture continually came into contact with the cork stopper as the mixture refluxed.

Normally the MDSA and its by-products are used as a crude mixture. Thus, use of MDSA as a strong acid catalyst or as a polymer intermediate to react with other difunctional materials does not require separation from the by-products. Moreover, recovery of the MDSA from the mixture adds to the expense of the process and may lead to decomposition.

If desired, however, the MDSA may be recovered from the equilibrium mixture by known methods. For example, methanedisulfonic acid can be obtained in a more pure form by vacuum stripping of the volatile by-products, preferably heating at 122° C. at 1.0 mm Hg (or 85° C. at 0.02 mm Hg) to remove methanesulfonic acid [b.p. 122° C. (1.0 mm Hg)], methanesulfonyl chloride [b.p. 53° C. (12.0 mm Hg)] and traces of chlorosulfonic acid [b.p. 60°–64° C. (2–4 mm Hg)]. Pure methanedisulfonic acid is a solid with a melting point of 96°–100° C. and is very hygroscopic.

The process of this invention has the advantage that methanedisulfonic acid is cleanly formed in a conversion of about 30 to 40% yield. Chlorosulfonic acid has a boiling point of 151–152 degrees Centigrade, and is much easier to handle than sulfur trioxide. In addition, compared to the sulfur trioxide process of U.S. Pat. No. 2,842,589, fewer by-products are observed using chlorosulfonic acid.

The invention will now be illustrated in further detail by reference to the following specific, non-limiting examples. Unless otherwise indicated the chemical shifts in the proton nuclear magnetic resonance ($H^1$nmr) analysis are relative to t-butyl alcohol (1.30 ppm).

EXAMPLE 1

To an Erlenmeyer flask with a loosely fitted cork stopper were added 9.6g (0.1 mole) of methanesulfonic acid (100%) and 11.7 g (0.1 mole) of chlorosulfonic acid. The mixture was stirred in a well-ventillated hood using a magnetic stirring bar, heated at 100 degrees Centigrade for 1 hour, cooled, and then weighed to give 13.0 g of a wet-looking solid. It was noticed that the above reaction mixture contained a small piece of cork which had fallen in and carbonized. The proton nuclear magnetic resonance ($H^1$nmr) analysis indicated:

| Chemical Shift (ppm) | Assignment | Conc. (mole %) |
| --- | --- | --- |
| 4.40 | Methanedisulfonic acid | 34.0 |
| 3.78 | Methanesulfonyl chloride | 10.4 |
| 2.86 | Methanesulfonic acid | 52.1 |
| 3.41 | Unknown (methanol?) | 3.5 |
| | | 100.0 |

EXAMPLE 2

Example 1 was repeated under the same conditions of reaction except no cork was present and 0.1 g of activated carbon was used to catalyze the reaction. Virtually identical $H^1$nmr data were obtained as in Example 1.

EXAMPLE 3

Example 1 was repeated under the same conditions of reaction except no cork or activated carbon was used. However, the flask was open to the air during the reaction period. The results indicated a lower concentration (4.9%) of methanedisulfonic acid after 2.5 hours of heating at 130–140 degrees Centigrade. The $H^1$nmr analysis was as follows:

| Chemical Shift (ppm) | Assignment | Conc. (mole %) |
| --- | --- | --- |
| 4.38 | Methanedisulfonic acid | 4.9 |
| 3.96 | Methanesulfonyl chloride | 23.2 |
| 2.87 | Methanesulfonic acid | 71.9 |
| | | 100.0 |

EXAMPLE 4

To an nmr pressure tube was added a portion of a mixture of 9.6 g (0.1 mole) of methanesulfonic acid (100%) and 11.6 g (0.1 mole) of chlorosulfonic acid. The mixture was heated for 8 hours at 140 degrees Centigrade after purging and blanketing with nitrogen. The $H^1$nmr indicated that the reaction mixture contained no methanedisulfonic acid, but instead contained methanesulfonyl chloride and methanesulfonic acid. The $H^1$nmr analysis was as follows:

| Chemical Shift (ppm) | Assignment | Conc. (mole %) |
| --- | --- | --- |
| 3.30 | Methanesulfonyl chloride | 57.4 |
| 2.82 | Methanesulfonic acid | 42.6 |
| | | 100.0 |

EXAMPLE 5

Example 1 was repeated using a loosely fitted cork and the same reaction conditions, but containing 0.2 mole chlorosulfonic acid and 0.1 methanesulfonic acid and heating for 1 hour at 140 degrees Centigrade to give a viscous liquid on cooling. The $H^1$nmr indicated:

| Chemical Shift (ppm) | Assignment | Conc. (mole %) |
| --- | --- | --- |
| 4.45 | Methanedisulfonic acid | 22.8 |
| 3.92 | Methanesulfonyl chloride | 20.6 |
| 3.45 | Unknown (Methanol?) | 4.7 |
| 2.90 | Methanesulfonic acid | 51.9 |
| | | 100.0 |

The present invention may be embodied in other specific forms without departing from the spirit or essential attributes thereof, and accordingly reference should be made to the appended claims, rather than the specification, as indicating the scope of the invention.

I claim:

1. A method for preparing an alkanedisulfonic acid comprising reacting chlorosulfonic acid with an alkanesulfonic acid.

2. A method according to claim 1 wherein said alkane is a $C_1$-$C_6$ alkane.

3. A method according to claim 2 wherein said alkane is methane.

4. A method according to claim 1 wherein the reactants are substantially anhydrous.

5. A method according to claim 1 wherein the reaction is carried out in the presence of oxygen.

6. A method according to claim 5 wherein the reaction atmosphere is air.

7. A method according to claim 1 wherein the reaction is carried out at substantially atmospheric pressure.

8. A method according to claim 1 wherein the reaction is carried out in the presence of a catalyst.

9. A method according to claim 8 wherein the catalyst is activated carbon.

10. A method according to claim 5 wherein the reaction is carried out in the presence of an activated carbon cocatalyst.

11. A method according to claim 8 wherein said catalyst is present in an amount of about 0.5 to 2 grams per mole of theoretical product.

12. A method according to claim 1 wherein the reaction is carried out at a temperature of about 70 to 160 degrees Centigrade.

13. A method according to claim 12 wherein the reaction is carried out at a temperature of about 100-160 degrees Centigrade.

14. A method according to claim 1 wherein the chlorosulfonic acid and methanesulfonic acid are present in a molar ratio of about 0.5:1 to about 3:1.

15. A method according to claim 14 wherein the molar ratio is about 1:1 to 1.5:1.

16. A method according to claim 14 wherein the reactants are present in an approximately equimolar ratio.

17. A method of preparing methanedisulfonic acid comprising reacting chlorosulfonic acid with methanesulfonic acid at substantially atmospheric pressure in the presence of air and substantially anhydrous conditions.

18. A method according to claim 17 wherein the reaction is carried out in the presence of an activated carbon catalyst.

19. A method according to claim 17 wherein the reaction is carried out at a temperature of about 100-160 degrees Centigrade.

20. A method according to claim 17 wherein the reactants are present in an approximately equimolar ratio.

* * * * *